United States Patent [19]

Edwards et al.

[11] Patent Number: 5,354,782
[45] Date of Patent: Oct. 11, 1994

[54] POLYAMINE PHENOLS AS RADIOPROTECTIVE AGENTS

[75] Inventors: Michael L. Edwards, Cincinnati; Ronald D. Snyder, Loveland, both of Ohio

[73] Assignee: Merrell Dow Pharmaceuticals Inc., Cincinnati, Ohio

[21] Appl. No.: 114,113

[22] Filed: Aug. 30, 1993

Related U.S. Application Data

[63] Continuation of Ser. No. 20,899, Feb. 22, 1993, abandoned, which is a continuation of Ser. No. 908,497, Jun. 30, 1992, abandoned, which is a continuation of Ser. No. 807,350, Dec. 18, 1991, abandoned, which is a continuation-in-part of Ser. No. 642,599, Jan. 17, 1991, abandoned.

[51] Int. Cl.$^5$ ............... C07C 211/14; C07C 211/54; A61K 31/135
[52] U.S. Cl. ................... 514/655; 514/654; 564/367; 564/368; 564/370; 564/371
[58] Field of Search ............... 564/367, 368, 370, 371; 514/654, 655, 917

[56] References Cited

U.S. PATENT DOCUMENTS

| | | | |
|---|---|---|---|
| 2,653,977 | 9/1953 | Craig et al. | 260/570.5 |
| 2,951,092 | 8/1960 | Sowinski et al. | 260/553 |
| 3,098,841 | 7/1963 | Morris et al. | 564/367 |
| 3,312,732 | 4/1967 | Gollis et al. | 514/917 |
| 3,396,905 | 2/1968 | Jones et al. | 96/107 |
| 3,527,804 | 9/1970 | Cyba | 564/368 |
| 3,944,397 | 3/1976 | Gardiner et al. | 44/58 |
| 3,960,959 | 6/1976 | Pless | 260/570.5 P |
| 4,028,416 | 6/1977 | Robin et al. | 260/570.58 |
| 4,046,765 | 9/1977 | Bar et al. | 514/917 |
| 4,629,722 | 12/1986 | Rubi | 514/917 |
| 4,847,267 | 7/1989 | Deckner et al. | 514/917 |
| 5,059,391 | 10/1991 | Botta et al. | 564/368 |
| 5,217,964 | 6/1993 | Edwards et al. | 514/104 |

FOREIGN PATENT DOCUMENTS

| | | |
|---|---|---|
| 0277635 | 8/1988 | European Pat. Off. . |
| 0294183 | 12/1988 | European Pat. Off. . |
| 0311068 | 4/1989 | European Pat. Off. . |
| 0349224 | 1/1990 | European Pat. Off. . |
| 0375668 | 6/1990 | European Pat. Off. . |
| 0404039 | 6/1990 | European Pat. Off. . |
| 0497202 | 8/1992 | European Pat. Off. . |
| 1645049 | 9/1976 | Fed. Rep. of Germany . |

OTHER PUBLICATIONS

Brown et al. "Can WR-2721 Be Improved Upon?" *Pharmac. Ther.* vol. 39, pp. 157-168, (1988).
Kovaleu et al. "Study of Inhibitors in Oxidation, etc." *Viniti* 443-82 1981 abst in *Chem Abst* 98(26): 163553v Columbus Ohio 1981.
M. L. Edwards et al., J. Med. Chem. 34, pp. 569-574 (1991).
Edwards and Snyder, U.S. patent application Ser. No. 07/644,810, filed Jan. 23, 1991.
Edwards and Snyder, U.S. patent application Ser. No. 07/644,701 filed Jan. 23, 1991.
T. R. Sweeney: A Survey of Compounds from the Antiradiation Drug Development Program of the U.S. Army Medical Research and Development Command. Walter Reed Army Institute of Research, Washington, D.C. (1979).
J. Van Alphen: Rec. Trav. Chim. 58, 544 (1939) and 59, 31 (1940).
Weiss and Simic: Pharmac. Ther. 39, 1 (1988).
Brown et al.: Pharmac. Ther. 39, 157 (1988).
Grdina et al.: Pharmac. Ther. 39, 21 (1988).

*Primary Examiner*—Peter O'Sullivan
*Attorney, Agent, or Firm*—T. Helen Payne

[57] ABSTRACT

The present invention relates to certain polyamine phenols which are useful as radioprotective agents.

14 Claims, No Drawings

POLYAMINE PHENOLS AS RADIOPROTECTIVE AGENTS

This is a continuation of application Ser. No. 08/020,899, now abandoned, filed Feb. 22, 1993, which is a continuation of application Ser. No. 07/908,497, filed Jun. 30, 1992, now abandoned, which is a continuation of application Ser. No. 07/807,350, filed Dec. 18, 1991, now abandoned, which is a continuation-in-part of application Ser. No. 07/642,599, filed Jan. 17, 1991, now abandoned.

BACKGROUND OF THE INVENTION

Radioprotective agents, also known as radioprotectors, are defined as agents which protect cells or organisms from deleterious cellular effects of exposure to ionizing radiation. These deleterious cellular effects include damage to cellular DNA, such as DNA strand break, disruption in cellular function, cell death, tumor induction and the like. The mechanism of this protective effect may at least partially be due to radical scavenging properties of the radioprotective agents.

The potential utility of these agents in protecting against exposure to environmental radiation, as well as in cancer radiation therapy, has long been recognized. These agents, administered prior to or during exposure, would eliminate or reduce the severity of deleterious cellular effects caused by exposure to environmental ionizing radiation such as resulting from a nuclear explosion, a spill of radioactive material, close proximity to radioactive material and the like.

In addition, these agents are believed to provide a selective protection of normal cells, and not of cancer cells, during cancer radiation therapy. For example, these agents, administered to the cancer patient prior to or during radiation therapy, will be absorbed by normal, non-cancer cells to provide a protective effect. However, the radioprotective agents will not be absorbed to the same extent by tumor cells due to the poor vascularity associated with the tumor. Therefore, the radioprotective agents would provide a selective protective effect on the normal cells as compared to tumor cells and would eliminate or reduce the severity of deleterious cellular effects of radiation therapy on normal cells. Furthermore, some radioprotective agents may act as prodrugs and require activation by cellular enzymatic processes which are not fully operative in the cancer cell. These agents, even if absorbed in a similar concentration in normal and cancer cells, will only be activated in cells with normal enzymatic processes and not in cancer cells. These prodrug radioprotective agents would be activated to provide a selective protective effect only in normal cells and would thus eliminate or reduce the severity of deleterious cellular effects of radiation therapy on normal cells.

Furthermore, certain radioprotective agents provide a selective protection against deleterious cellular effects in normal cells caused by certain DNA-reactive agents such as cisplatin, cyclophosphamide, diethylnitrosoamine, benzo(a)pyrene, carboplatin, doxorubicin, mitomycin-C and the like. Many of these DNA-reactive agents are chemotherapeutic agents useful in cancer therapy. Radioprotective agents are useful in eliminating or reducing the severity of deleterious effects in normal cells caused by exposure to these DNA-reactive agents, such as during cancer therapy with DNA-reactive chemotherapeutic agents.

In addition, certain radioprotective agents provide a selective protection against therapy-induced secondary tumor induction [See Grdina et al., Pharmac. Ther. 39, 21 (1988)]. Radiation and chemotherapy provide effective treatments for a variety of neoplastic disease states. Unfortunately, these treatments themselves are oftentimes mutagenic and/or carcinogenic and result in therapy-induced secondary tumor induction. For example, patients treated for Hodgkin's disease appear to exhibit a relatively high risk for therapy-induced acute myelogenous leukemia and non-Hodgkin's lymphoma. Radioprotective agents provide selective protection against deleterious cellular effects, such as tumor induction, caused by radiation therapy or chemotherapy with a DNA-reactive chemotherapeutic agent. Radioprotective agents are thus useful in eliminating or reducing the risk of secondary tumor induction brought about by radiotherapy or chemotherapy.

Radioprotective agents thus are useful in eliminating or reducing the severity of deleterious cellular effects in normal cells caused by environmental exposure to ionizing radiation, cancer radiation therapy and treatment with DNA-reactive chemotherapeutic agents. See generally, Weiss and Simic, Pharmac. Ther. 39, 1 (1988).

The prototypical radioprotective agent, developed by the Antiradiation Drug Development Program at the Walter Reed Army Institute of Research, is WR-2721, or S-2(3-aminopropylamino)ethylphosphorothioic acid, which has the structure

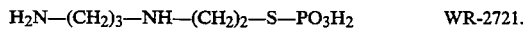

$$H_2N-(CH_2)_3-NH-(CH_2)_2-S-PO_3H_2 \qquad \text{WR-2721.}$$

Other known radioprotective agents are WR-1065, thought to be a metabolite of WR-2721, which has the structure

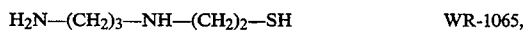

$$H_2N-(CH_2)_3-NH-(CH_2)_2-SH \qquad \text{WR-1065,}$$

and WR-151,327, which has the structure

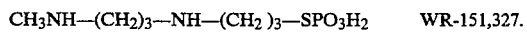

$$CH_3NH-(CH_2)_3-NH-(CH_2)_3-SPO_3H_2 \qquad \text{WR-151,327.}$$

SUMMARY OF THE INVENTION

The present invention provides novel radioprotective agents of the formula (1)

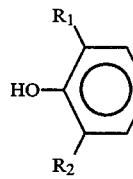 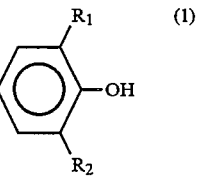

$$HO-\underset{R_2}{\overset{R_1}{\text{C}_6H_2}}-(CH_2)_n-NH-Z-NH(CH_2)_m-NH-Z-NH-(CH_2)_n-\underset{R_2}{\overset{R_1}{\text{C}_6H_2}}-OH \quad (1)$$

wherein
R$_1$ and R$_2$ are each independently a C$_1$–C$_6$ alkyl group,
n is an integer from 0 to 3,
Z is a C$_2$–C$_6$ alkylene group, and m is an integer from 4 to 9.

The present invention further provides novel radio-protective agents of the formula (2)

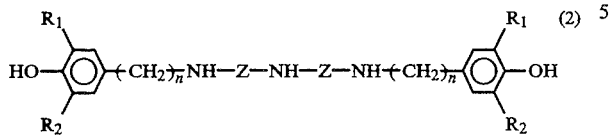

wherein $R_1$ and $R_2$ are each independently a $C_1$-$C_6$ alkyl group, n is an integer 0 to 3, and Z is a $C_2$-$C_6$ alkylene group.

In addition, the present invention provides a method of protecting mammalian cells from deleterious cellular effects caused by exposure to ionizing radiation or to a DNA-reactive agent comprising contacting said cells with a protective amount of a compound of formula (1) or (2).

The present invention also provides a method of protecting non-cancer cells of a human from deleterious cellular effects caused by exposure to ionizing radiation or by exposure to a DNA-reactive agent comprising administering to said human a protective amount of a compound of formula (1) or (2).

The present invention further provides a method of treating a patient in need of radiation therapy, or in need of chemotherapy with a DNA-reactive chemotherapeutic agent, comprising administering to said patient a protective amount of a compound of formula (1) or (2).

DETAILED DESCRIPTION OF THE INVENTION

As used herein, the following terms have the meanings as indicated below:

(1) the term "$C_1$-$C_6$ alkyl" refers to a saturated straight or branched chain hydrocarbyl radical of one to six carbon atoms. Included within the scope of this term are methyl, ethyl, n-propyl, isopropyl, n-butyl, isobutyl, sec-butyl, t-butyl, n-pentyl, n-hexyl and the like;

2) The term "$C_2$-$C_6$ alkylene" refers to a saturated hydrocarbylene radical of from 2 to 6 carbon atoms of straight chain configuration. Specifically included within the scope of the term are the radicals —$CH_2CH_2$—, —$CH_2CH_2CH_2$—, —$CH_2(CH_2)_2CH_2$—, $CH_2(CH_2)_3CH_2$—, —$CH_2(CH_2)_4CH_2$—;

3) The term "halo" or the term "Hal" refers to a chlorine, bromine or iodine atom;

4.) The term "Ts" refers to a tosylate functionality of the formula:

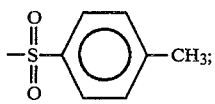

5) The term "BOC" refers to a t-butyloxycarbonyl functionality of the formula:

The compounds of formula (1) wherein n=1 can be prepared by utilizing procedures and techniques well known and appreciated by one of ordinary skill in the art. A general synthetic scheme for preparing these compounds is set forth in Scheme A wherein all substituents, unless otherwise indicated, are previously defined.

Scheme A

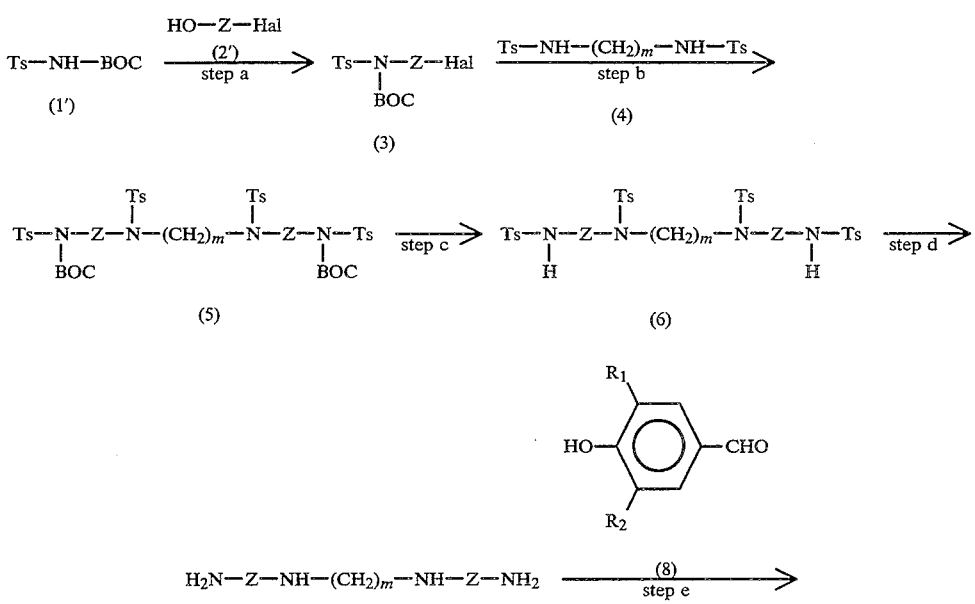

-continued
Scheme A

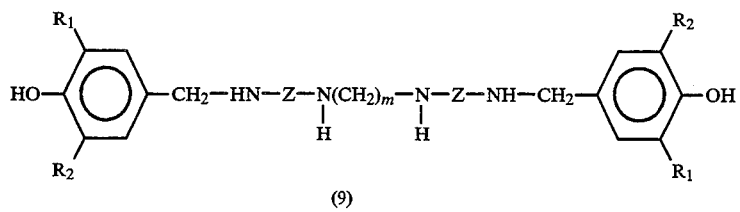

(9)

Scheme A provides a general synthetic scheme for preparing compounds of formula (1) wherein n=1.

In step a, N-(t-butyloxycarbonyl)-N-[(4-methylphenyl)sulfonamide] (1') is alkylated with an appropriate haloalkanol of structure (2') to give the appropriate N-(t-butyloxycarbonyl)-N-[(4-methylphenyl)sulfonyl]-haloalkylamine of structure (3).

For example, N-(t-butyloxycarbonyl)-N-[(4-methylphenyl)sulfonamide] (1') is contacted with a molar equivalent of triphenylphosphine, a molar equivalent of the appropriate haloalkanol of structure (2') and a molar equivalent of diethyl azodicarboxylate. The reactants are typically contacted in a suitable organic solvent such as tetrahydrofuran. The reactants are typically stirred together at room temperature for a period of time ranging from 2–24 hours. The N-(t-butyloxycarbonyl)-N-[(4-methylphenyl)sulfonyl]-haloalkylamine of structure (3) is recovered from the reaction zone by evaporation of the solvent. It can be purified by silica gel chromatography.

In step b, the alkyl halide functionality of the appropriate N-(t-butyloxycarbonyl)-N-[(4-methylphenyl)sulfonyl]-haloalkylamine of structure (3) is aminated with the appropriate bis[(4-methylphenyl)sulfonyl]-diazaalkane of structure (4) to give the appropriate bis(t-butyloxycarbonyl)-tetra[(4-methylphenyl)sulfonyl]-tetraazaalkane of structure (5).

For example, the appropriate his[(4-methylphenyl)-sulfonyl]-diazaalkane of structure (4) is contacted with 2 molar equivalents of a non-nucleophilic base such as sodium hydride. The reactants are typically contacted in a suitable organic solvent such as dimethylformamide. The reactants are typically stirred together until evolution of hydrogen ceases at a temperature range of from 0° C. to room temperature. The appropriate N-(t-butyloxycarbonyl)-N-[(4-methylphenyl)sulfonyl]-haloalkylamine of structure (3) is then added to the reaction mixture. The reactants are typically stirred together for a period of time ranging from 2–24 hours and at a temperature range of from 0° C. to 50° C. The bis(t-butyloxycarbonyl)-tetra[(4-methylphenyl)sulfonyl]-tetraazaalkane of structure (5) is recovered from the reaction zone by extractive methods as is known in the art. It can be purified by silica gel chromatography.

In step c, the t-butyloxycarbonyl functionalities of the appropriate bis(t-butyloxycarbonyl)-tetra[(4-methylphenyl)sulfonyl]-tetraazaalkane of structure (5) are hydrolyzed to give the appropriate tetra[(4-methylphenyl)sulfonyl]-tetraazaalkane of structure (6).

For example, the appropriate bis(t-butyloxycarbonyl)tetra[(4-methylphenyl)sulfonyl]-tetraazaalkane of structure (5) is contacted with a molar excess of an acid, such as hydrochloric acid. The reactants are typically contacted in a suitable protic organic solvent, such as methanol. The reactants are typically stirred together for a period of time ranging from 2–24 hours and at a temperature range of from 0° C. to room temperature.

The tetra[(4-methylphenyl)sulfonyl]-tetraazaalkane of structure (6) is recovered from the reaction zone by extractive methods as is known in the art. It can be purified by silica gel chromatography.

In step d, the sulfonamide functionalities of the appropriate tetra[(4-methylphenyl)sulfonyl]-tetraazaalkane of structure (6) are cleaved to give the appropriate tetraazaalkane of structure (7).

For example, the appropriate tetra[(4-methylphenyl)-sulfonyl]-tetraazaalkane of structure (6) is contacted with a molar excess of sodium in liquid ammonia. The reactants are typically stirred together at a temperature range of from −40° C. to −20° C. for a period of time ranging from 1–10 hours. The tetraazaalkane of structure (7) is recovered from the reaction zone by evaporation of the ammonia. It can be purified by silica gel chromatography.

In step e, the terminal amino functionalities of the appropriate tetraazaalkane of structure (7) are reductively alkylated with the appropriate 4-hydroxybenzaldeyde of structure (8) to give the appropriate bis[(4-hydroxyphenyl)methyl]-tetraazaalkane of structure (9).

For example, the appropriate tetraazaalkane of structure (7) is contacted with 2 molar equivalents of an appropriate 4-hydroxybenzaldehyde of structure (8), a molar excess of sodium cyanoborohydride and a catalytic amount of an acid-base indicator, such as bromocresol green. The reactants are typically contacted in a suitable protic organic solvent, such as ethanol. The reactants are typically stirred together while a suitable acid, such as hydrochloric acid, is added in order to maintain a slightly acidic medium as indicated by a yellow color. The reactants are typically stirred together at room temperature for a period of time necessary for the color to remain yellow. The bis[(4-hydroxyphenyl)methyl]tetraazaalkane of structure (9) is recovered from the reaction zone by extractive methods as is known in the art.

The bis[(4-hydroxyphenyl)methyl]-tetraazaalkane of structure (9) is purified by first converting the free amino functionalities to their corresponding t-butyloxycarbonamides with 4 molar equivalents of di-tert-butyldicarbonate. The reactants are typically contacted in a miscible organic solvent/aqueous base solvent mixture such as dioxane/sodium hydroxide. The reactants are typically stirred together at room temperature for a period of time ranging from 1–10 hours. The bis[(4-hydroxyphenyl)methyl]-bis(t-butyloxycarbonyl)tetraazaalkane is recovered from the reaction zone by extractive methods as is known in the art. It can be purified by silica gel chromatography. The t-butylcarboxamide functionalities of the purified bis[(4-hydroxyphenyl)methyl]-bis(t-butyloxycarbonyl)tetraazaalkane are then hydrolyzed with methanolic hydrochloric acid to give the purified bis[(4-hydroxyphenyl)methyl]-tetraazaalkane of structure (9) as its tetrahydrochloride salt.

Starting materials for use in the general synthetic procedures outlined in Scheme A are readily available to one of ordinary skill in the art. For example, N-(t-butyloxycarbonyl)-N-[(4-methylphenyl)sulfonamide] is described in *Tetrahedron Lett.*, 30, 5709–12 1989.

The following example presents a typical synthesis as described in Scheme A. This example is understood to be illustrative only and is not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "µL" refers to microliters; "µg" refers to micrograms; and "µM" refers to micromolar.

EXAMPLE 1

1,19-Bis[(3,5-di-t-butyl-4-hydroxyphenyl)methyl]-1,6,14,19-tetraazanonadecane, tetrahydrochloride Step a:
N-(t-Butyloxycarbonyl)-N-[(4-methylphenyl)sulfonyl]-4-chlorobutylamine Dissolve N-(t-butyloxycarbonyl)-N-[(4-methylphenyl)sulfonamide](88 mg, 0.322 mmol) in anhydrous tetrahydrofuran (3mL) and add triphenylphosphine (84 mg, 0.322 mmol). Stir under a nitrogen atmosphere and add 4-chloro-1-butanol (34.9 mg, 0.322 mmol) followed by diethyl azodicarboxylate (0.050 mL, 0.322 mmol). Stir at room temperature for several hours and evaporate the solvent vacuo. Purify by silica gel chromatography to give the title compound.

Step b:
1,19-Bis(t-Butyloxycarbonyl)-1,6,14,19-tetra[(4-methylphenyl)sulfonyl]-1,6,14,19-tetraazanonadecane Dissolve 1,9-diazanonane (13g, 0.1 mol) in pyridine (50 mL) and cool to ° C. Add, in portions, p-toluenesulfonyl chloride (41.9 g, 0.22 mol) and stir overnight. Extract into chloroform, wash with water, 5% hydrochloric acid, water and dry (MgSO4). Evaporate the solvent in vacuo and purify by silica gel chromatography to give 1,9-bis[(4-methylphenyl)sulfonyl]-1,9-diazanonane.

Suspend sodium hydride (4.8 g, 0.2 mol) in anhydrous dimethylformamide (100 mL), cool to 0° C. and place under a nitrogen atmosphere. Add, by dropwise addition, a solution 1,9-bis[(4-methylphenyl)sulfonyl]-1,9-diazanonane (43.8 g, 0.1 mol) in dimethylformamide. Stir until evolution of hydrogen ceases. Add, by dropwise addition, a solution of N-(t-butyloxycarbonyl)-N-[(4-methylphenyl)sulfonyl]-4-chlorobutylamine (72.4 g, 0.2 mol) in dimethylformamide (100 mL). Stir overnight at room temperature then carefully quench with saturated ammonium chloride. Extract into ethyl acetate, dry (MgSO4) and evaporate the solvent in vacuo. Purify by silica gel chromatography to give the title compound.

Step c:
1,6,14,19-Tetra[(4-methylphenyl)sulfonyl]-1,6,14,19-tetraazanonadecane

Dissolve 1,19-bis(t-butyloxycarbonyl)-1,6,14,19-tetra[(4-methylphenyl)sulfonyl]-1,6,14,19-tetraazanonadecane (11.7 g, 10 mmol) in saturated methanolic hydrochloric acid (100 mL). Stir for several hours and evaporate the solvent in vacuo. Dissolve the residue in water and neutralize with saturated sodium hydrogen carbonate and extract with ethyl acetate. Dry (MgSO4) and evaporate the solvent in vacuo. Purify by silica gel chromatography to give the title compound.

Step d: 1,6,14,19-Tetraazanonadecane

Mix 1,6,14,19-tetra[(4-methylphenyl)sulfonyl]-1,6,14,19-tetraazanonadecane (3.9 g, 4 mmol) in dry liquid ammonium (25 mL) at −40° C. Add small pieces of sodium until a permanent blue color remains. Discharge the excess sodium with saturated ammonium chloride. Allow the ammonia to evaporate spontaneously and partition the residue between ethyl acetate and water. Separate the organic phase, dry (MgSO4) and evaporate the solvent in vacuo. Purify by silica gel chromatography to give the title compound.

Step e:
1,19-Bis[(3,5-di-t-butyl-4-hydroxyphenyl)methyl]-1,6,14,19-tetraazanonadecane, tetrahydrochloride Dissolve 1,6,14,19-tetraazanonadecane (1.35 g, 0.005 mol) in methanol (distilled from Mg) (50 mL) and add 3,5-di-t-butyl-4-hydroxybenzadehyde (2.34 g, 0.01 mol), sodium cyanoborohydride (0.62 g, 0.010 mol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (50 mL) and ethyl acetate (100 mL). Separate the organic phase, dry (MgSO4) and evaporate the solvent in vacuo give the crude product.

Dissolve the crude 1,19-bis[(3,5-di-t-butyl-4-hydroxyphenyl)methyl]-1,6,14,19-tetraazanonadecane (3.54 g, 5 mmol) in 50/50 dioxane/water (25 mL) and buffer to pH 10 with 1N sodium hydroxide. Add, by dropwise addition, an ether solution of di-t-butyl dicarbonate (4.8 g, 22 mmol) at 10° C. Allow to warm to room temperature and buffer occasionally to retain pH 10. Acidify with a sodium citrate/citric acid buffer to pH 5, extract with ether (3X), dry (MgSO4) and evaporate the solvent in vacuo. Purify the residue by silica gel chromatography to give 1,19-bis[(3,5-di-t-butyl-4-hydroxyphenyl)methyl]-1,6,14,19-tetra(t-butyloxycarbonyl)-1,6,14,19-tetraazanonadecane.

Dissolve 1,19-bis[(3,5-di-t-butyl-4-hydroxyphenyl)-methyl]-1,6,14,19-tetra(t-butyloxycarbonyl)-1,6,14,19-tetraazanonadecane (10.8 g, 10 mmol) in saturated methanolic hydrochloric acid (100 mL). Stir for several hours and evaporate the solvent in vacuo give the title compound.

The following compounds can be prepared analogously to that described in Example 1:
1,16-Bis[(3,5-di-t-butyl-4-hydroxyphenyl)methyl]-1,5,12,16-tetraazahexadecane, tetrahydrochloride;
1,18-Bis[(3,5-di-t-butyl-4-hydroxyphenyl)methyl]-1,5,14,18-tetraazaoctadecane, tetrahydrochloride.

The compounds of formula (1) wherein n=0, 2, or 3 can be prepared by utilizing procedures and techniques well known and appreciated by one of ordinary skill in the art. A general synthetic scheme for preparing these compounds is set forth in Scheme B wherein all substituents, unless otherwise indicated, are previously defined.

Scheme B

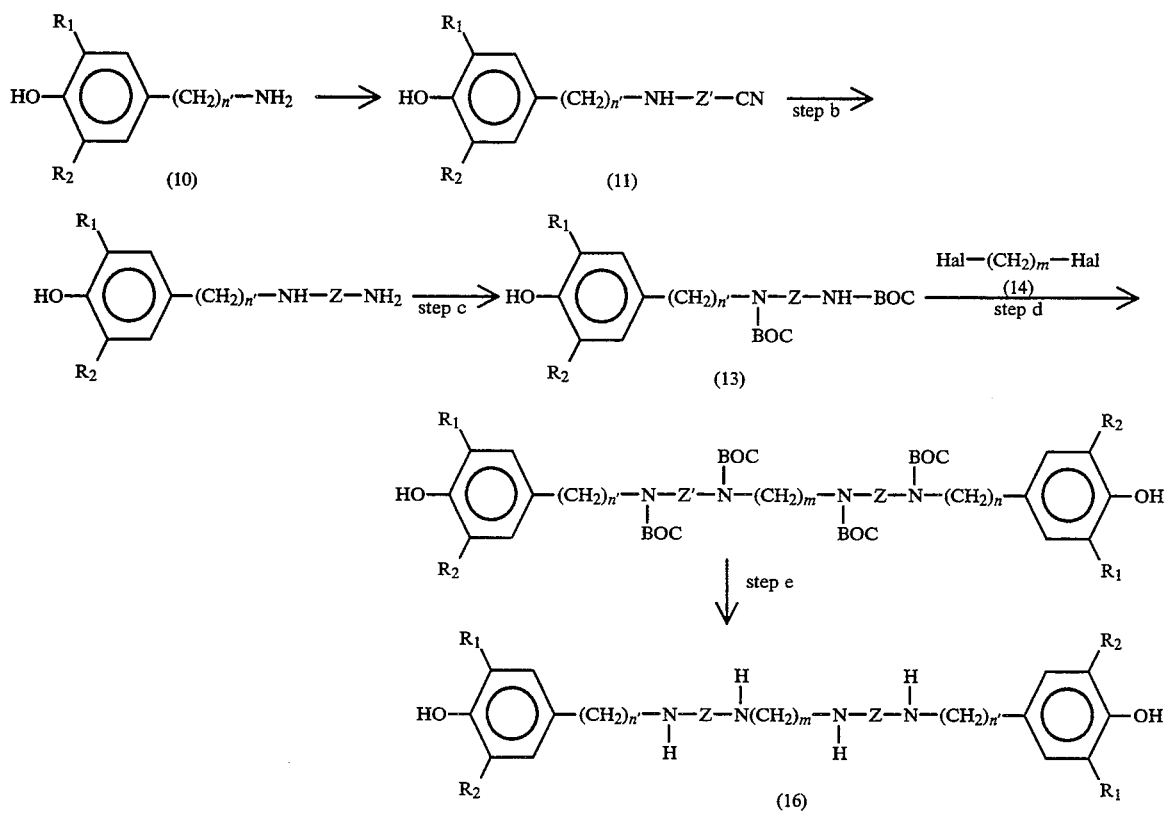

Z' = Z minus CH₂
n' = 0, 2, or 3

Scheme B provides a general synthetic scheme for preparing compounds of formula (1) wherein n=0, 2, or 3.

In step a, the nitrogen functionality of an appropriate (4-hydroxyphenyl)alkylamine of structure (10) is alkylated to give the appropriate [(4-hydroxyphenyl)alkylamino]alkylnitrile of structure (11). Appropriate alkylating agents would be those which contain a nitrile functionality. For example, if the desired compound of formula (1) is one in which Z is represented by a $C_3$ alkylene group, an appropriate alkylating agent would be acrylonitrile. If the desired compound of formula (1) is one in which Z is represented by a $C_2$ or a $C_4$–$C_6$ alkylene group, appropriate alkylating agents would be the corresponding haloalkylnitriles.

For example, an appropriate (4-hydroxyphenyl)alkylamine of structure (10) is contacted with a molar excess of an appropriate alkylating agent. The reactants are typically contacted in a suitable protic organic solvent, such as ethanol. The reactants are typically stirred together for a period of time ranging from 5–24 hours and at a temperature range of from room temperature to reflux. The [(4-hydroxyphenyl)alkylamino]-alkylnitrile of structure (11) is recovered from the reaction zone by evaporation of the solvent. It can be purified by distillation or silica gel chromatography.

In step b, the nitrile functionality of the appropriate [(4-hydroxyphenyl)alkylamino]-alkylnitrile of structure (11) is reduced to give the [(4-hydroxyphenyl)alkyl]-diazaalkane of structure (12).

For example, the appropriate [(4-hydroxyphenyl)alkylamino]-alkylnitrile of structure (11) is contacted with a molar excess of a reducing agent, such as lithium aluminum hydride. The reactants are typically contacted in a suitable organic solvent, such as ethyl ether. The reactants are typically stirred together at room temperature for a period of time ranging from 2–24 hours. The [(4-hydroxyphenyl)alkyl]-diazaalkane of structure (12) is recovered from the reaction zone by extractive methods as is known in the art. It can be purified by silica gel chromatography.

In step c, the amino functionalities of the appropriate (4-hydroxyphenyl)alkyl]-diazaalkane of structure (12) are protected as the t-butyloxycarbonyl derivatives to give the corresponding [(4-hydroxyphenyl)alkyl]-bis(t-butyloxycarbonyl)diazaalkane of structure (13).

For example, the appropriate [(4-hydroxyphenyl)alkyl]diazaalkane of structure (12) is contacted with 2 molar equivalents of an appropriate t-butyloxycarbonylating agent such as di-t-butyldicarbonate. The reactants are typically contacted in a miscible organic solvent/aqueous base mixture such as dioxane/sodium hydroxide. The reactants are typically stirred together at room temperature for a period of time ranging from 1–10 hours. The [(4-hydroxyphenyl)-alkyl]-bis(t-butyloxycarbonyl)diazaalkane of structure (13) is recovered from the reaction zone by extractive methods as is known in the art. It can be purified by silica gel chromatography.

In step d, the terminal t-butyloxycarbamide functionality of the appropriate [(4-hydroxyphenyl)alkyl]bis(t-butyloxycarbonyl)-diazaalkane of structure (13) is alkylated with an appropriate dihaloalkane of structure

(14) to give the bis[(4-hydroxyphenyl)alkyl]-tetra(t-butyloxycarbonyl)-tetraazaalkane of structure (15).

For example, the appropriate [(4-hydroxyphenyl)alkyl]bis(t-butyloxycarbonyl)-diazaalkane of structure (13) is contacted with 2 molar equivalents of a non-nucleophilic base such as sodium hydride. The reactants are typically contacted in a suitable organic solvent such as dimethylformamide. The reactants are typically stirred together until evolution of hydrogen ceases at a temperature range of from 0° C. to room temperature. The appropriate dihaloalkane of structure (14) is then added to the reaction mixture. The reactants are typically stirred together for a period of time ranging from 2–24 hours and at a temperature range of from 0° C. to room temperature. The bis[(4-hydroxyphenyl)alkyl]-tetra(t-butyloxycarbonyl)tetraazaalkane of structure (15) is recovered from the reaction zone by extractive methods as is known in the art. It can be purified by silica gel chromatography.

In step e, the t-butyloxycarbonamide functionalities of the appropriate bis[(4-hydroxyphenyl)alkyl]-tetra(t-butyloxycarbonyl)-tetraazaalkane of structure (15) are hydrolyzed to give the corresponding bis[(4-hydroxyphenyl)alkyl]-tetraazaalkane of structure (16) as described previously in Scheme A, step c.

Starting materials for use in Scheme B are readily available to one of ordinary skill in the art. For example, 2,6-di-t-butyl-4-aminophenol is described in *Tetrahedron*, 18, 61 1962.

The following example presents a typical synthesis as described in Scheme B. This example is illustrative only and is not intended to limit the scope of the present invention in any way.

EXAMPLE 2

1,15-Bis[(3,5-di-t-butyl-4-hydroxyphenyl)]-1,5,11,15-tetraazapentadecane, tetrahydrochloride Step a:
3N-[3,5-Di-t-butyl-4-hydroxyphenyl]-3-aminopropionitrile Dissolve 2,6-di-t-butyl-4-aminophenol (41 g, 0.185 mol) and acrylonitrile (11.7 g, 0.22 mol) in ethanol (700 mL) and heat at reflux for 18 hours. Evaporate the solvent in vacuo and purify by distillation to give the title compound.

Step b:
1-[(3,5-Di-t-butyl-4-hydroxyphenyl)]-1,5-diazapentane

Suspend lithium aluminum hydride (2.1 g, 0.054 mol) in ether (250 mL). Add, by dropwise addition, a solution of aluminum chloride (7.3 g, 0.054 mol) in ether (250 mL). Stir for 20 minutes and add a solution of 3N-[3,5-di-t-butyl-4-hydroxyphenyl]-3-aminopropionitrile (14.7 g, 0.054 mol) in ether (25 mL). Stir at ambient temperature for 18 hours. Decompose the reducing agent by carefully adding water (20 mL) and 30% aqueous potassium hydroxide (100 mL). Filter and evaporate the solvent in vacuo and purify by silica gel chromatography to give the title compound.

Step c:
1-[(3,5-Di-t-butyl-4-hydroxyphenyl)]-1,5-bis(t-butyloxycarbonyl)-1,5-diazapentane Dissolve 1-[(3,5-di-t-butyl-4-hydroxyphenyl)]-1,5-diazapentane (1.39 g, 5 mmol) in 50/50 dioxane/water (25 mL) and buffer to pH 10 with 1N sodium hydroxide. Add, by dropwise addition, an ether solution of di-t-butyl dicarbonate (2.4 g, 11 mmol) at 10° C. Allow to warm to room temperature and buffer occasionally to retain pH 10. Acidify with a sodium citrate/citric acid buffer to pH 5, extract with ether (3X), dry (MgSO4) and evaporate the solvent in vacuo. Purify the residue by silica gel chromatography to give the title compound.

Step d:
1,15-Bis[(3,5-di-t-butyl-4-hydroxyphenyl)]-1,5,11,15-tetra(t-butyloxycarbonyl)-1,5,11,15-tetraazapentadecane Suspend sodium hydride (48 mg, 2 mmol) and anisole (215 mg, 2 mmol) in anhydrous dimethylformamide (2 mL), cool to 0° C. and place under a nitrogen atmosphere. Add, by dropwise addition, a solution 1-[(3,5-di-t-butyl-4-hydroxyphenyl)]-1,5-bis(t-butyloxycarbonyl)-1,5-diazapentane (1.91 g, 4 mmol) in dimethylformamide (2 mL). Stir until evolution of hydrogen ceases. Add, by dropwise addition, a solution of 1,5-dibromopentane (230 mg, 1 mmol) in dimethylformamide (2 mL). Stir overnight at room temperature then carefully quench with saturated ammonium chloride. Extract into ethyl acetate, dry (MgSO4) and evaporate the solvent in vacuo. Purify by silica gel chromatography to give the title compound.

Step e:
1,15-Bis[(3,5-di-t-butyl-4-hydroxyphenyl)]-1,5,11,15-tetraazapentadecane, tetrahydrochloride Dissolve 1,15-bis[(3,5-di-t-butyl-4-hydroxyphenyl)]-1,5,11,15-tetra(t-butyloxycarbonyl)-1,5,11,15-tetraazapentane (10.24 g, 10 mmol) in saturated methanolic hydrochloric acid (100 mL). Stir for several hours and evaporate the solvent in vacuo to give the title compound.

The following compounds may be prepared analogously to that described in Example 2:
1,19-Bis[(3,5-di-t-butyl-4-hydroxyphenyl)ethyl]-1,6,14,19-tetraazanonadecane, tetrahydrochloride;
1,18-Bis[(3,5-di-t-butyl-4-hydroxyphenyl)]-1,5,14,18-tetraazaoctadecane, tetrahydrochloride;
1,19-Bis[(3,5-di-t-butyl-4-hydroxyphenyl)propyl]-1,6,14,19-tetraazanonadecane, tetrahydrochloride.

The compounds of formula (2) wherein n=1, 2 or 3 can be prepared by utilizing procedures and techniques well known and appreciated by one of ordinary skill in the art. A general synthetic scheme for preparing these compounds is set forth in Scheme C wherein all substituents, unless otherwise indicated, are previously defined.

Scheme C

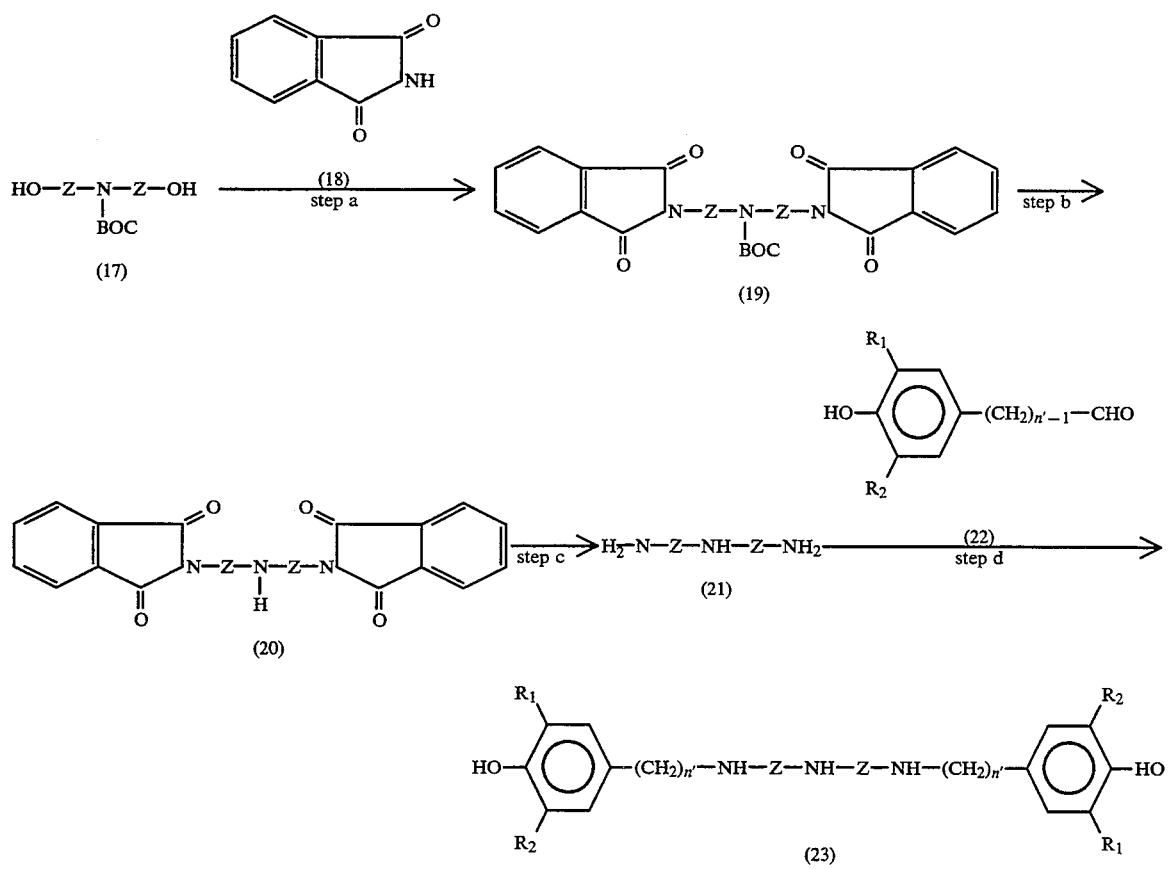

n = 1, 2 or 3

Scheme C provides a general synthetic scheme for preparing compounds of formula (2) wherein n=1, 2 or 3.

In step a, the appropriate bis(hydroxyalkyl)-t-butyl-carboxamide of structure (17) is reacted with phthalimide (18) under Mitsunobu conditions to give the corresponding bis[(3-(1,3-dihydro-1,3-dioxo-2H-isoindol-2-yl)]-t-butyloxycarboxamide of structure (19).

For example, the bis(hydroxyalkyl)-t-butyloxycarboxamide of structure (17) is contacted with 2 molar equivalents of phthalimide (18), 2 molar equivalents of triphenylphosphine and 2 molar equivalents of diethyl azodicarboxylate. The reactants are typically contacted in a suitable organic solvent, such as tetrahydrofuran. The reactants are typically stirred together for a period of time ranging from 10 minutes to 5 hours. The bis[(3-(1,3-dihydro-1,3-dioxo-2H-isoindol-2-yl)]-t-butyloxycarboxamide of structure (19) is recovered from the reaction zone by evaporation of the solvent. It can be purified by silica gel chromatography.

In step b, the t-butyloxycarbonyl functionality of the appropriate bis[(3-(1,3-dihydro-1,3-dioxo-2H-isoindol-2-yl)]-t-butyloxycarboxamide of structure (19) is hydrolyzed to give the corresponding bis[3-(1,3-dihydro-1,3-dioxo-2H-isoindol-2-yl))amine of structure (20) as described previously in Scheme A, step c.

In step c, the phthalimide functionalities of the appropriate bis [3-(1,3-dihydro-1,3-dioxo-2H-isoindol-2-yl)]amine of structure (20) are removed to give the corresponding triazaalkane of structure (21).

For example, the appropriate bis[3-(1,3-dihydro-1,3-dioxo-2H-isoindol-2-yl)]amine of structure (20) is contacted with 2 molar equivalents of hydrazine. The reactants are typically contacted in a suitable protic organic solvent such as methanol. The reactants are typically stirred together at reflux temperature for a period of time ranging from 2–24 hours. The triazaalkane of structure (21) is recovered from the reaction zone by extractive methods as is known in the art. It can be purified by silica gel chromatography.

In step d, the terminal amino functionalities of the appropriate triazaalkane of structure (21) are reductively aminated with the appropriate phenylalkylaldehyde of structure (22) to give the appropriate bis[(-phenyl)alkyl)triazaalkane of structure (23) as described previously in Scheme A, step e.

Starting materials for use in Scheme C are readily available to one of ordinary skill in the art.

The following example presents a typical synthesis as described in Scheme C where the triazaalkane (21) and the appropriate phenylalkylaldehyde (22) are commercially available.

EXAMPLE 3

1,9-Bis [(3,5-di-t-butyl-4-hydroxyphenyl)methyl]-1,5,9-triazanonane, trihydrochloride Step d:
1,9-Bis[(3,5-di-t-buyl-4-hydroxphenyl)methyl]-1,5,9-triazanonane, trihydrochloride Dissolve 1,5,9-triazanonane (2.6 g, 0.02 mol) in methanol (200 ml) (distilled from Mg). Add 3,5-di-t-butyl-4-hydroxybenzadehyde (18.8 g, 0.08 mol), sodium cyanoborohydride (0.5 g, 0.08 mol) and 1 drop of 1% bromocresol green in ethanol. Add 1N hydrochloric acid in methanol until the indicator turns from blue to yellow. Maintaining the acidity of the reaction mix for 3 hours. Add additional 3,5-di-t-butyl-4-hydroxybenzaldehyde 10 g(0.04 mol) and sodium cyanoborohydride (2.5 g, 0.04 mol). Evaporate the solvent in vacuo. Add tetrahydrofuran (200 ml). Make the solution basic with 1N sodium hydroxide. Cool the solution to 10° C. and add dropwise an ether solution of di-t-butyl dicarbonate (17.4 g, 0.08 mol).

Allow the mixture to warm to room temperature and buffer occasionally to retain basicity. Evaporate the solvent in vacuo. Redissolve the residue in methylene chloride (200 ml), extract with 1N HCl. Separate the organic layer, evaporate the solvent in vacuo and purify the residue with column chromatotography using silicagel to give 1,9-bis[3,5-di-t-butyl-4-hydroxyphenyl)methyl]-1,5,9-tri(t-butyloxcarbonyl)-1,5,9-triazanonane. Yield (3.6 g). Analysis for $C_{51}H_7SN_3O_8.0.87C_7H_8$. Theory C %=72.31,H %=9.77,N %=4.43; Found C %=72.22,H %=9.92,N %=4.62.

Dissolve 1,9-bis[(3,5-di-t-butyl-4-hydroxyphenyl)methyl]-1,5,9-tri(t-butyloxycarbonyl)-1,5,9-triazanonane (3.6 g, 4.1 mol) in methanol (50 ml). Add a solution of hydrochloric acid in methanol (50 ml, 1N). Stir for several hours. Then evaporate the solvent in vacuo to give the title compound. Redissolve the residue in warm 2-propanol (150 ml). Allow the product to crystallize. Separate the solid. Repeate the crystallization. Dry the title product in vacuo. Yeild (1.6 g). Analysis for $C_{36}H_{61}N_3O_2.3HCl.0.75$ $H_2O$. Theory C %=62.59,H %=9.56,N %=6.08,Cl%=15.40,$H_2O$%=2.0; Found C %-62.28,%-62.28,H %=9.62,N %=5.93, (Micro No. 910486). Spectra NMR,IR,MS, (91-0989).

The following compounds can be prepared analogously to that described in Example 3:

1,11-Bis[(3,5-di-t-butyl-4-hydroxyphenyl)ethyl]-1,6,11-triazaundecane, trihydrochloride;

1,9-Bis[(3,5-di-t-butyl-4-hydroxyphenyl)propyl]-1,5,9-triazanonane, trihydrochloride.

The compounds of formula (2) wherein n=0 can be prepared by utilizing procedures and techniques well known and appreciated by one of ordinary skill in the art. A general synthetic scheme for preparing these compounds is set forth in Scheme D wherein all substituents, unless otherwise indicated, are previously defined.

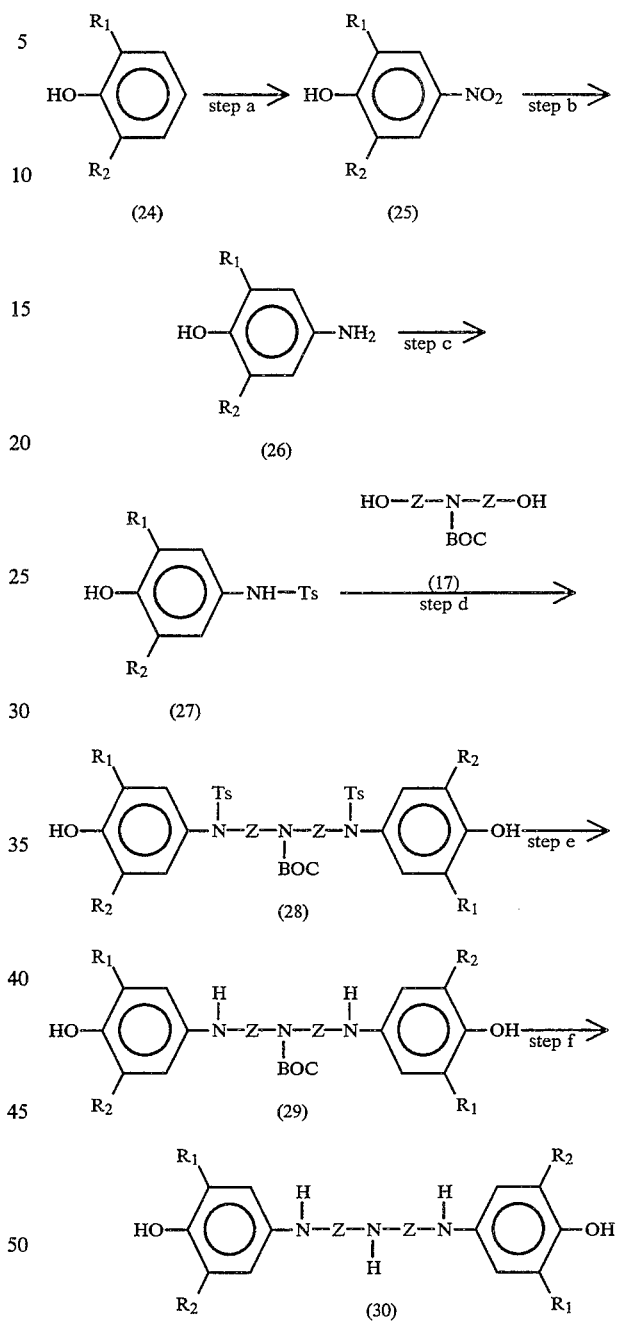

Scheme D

Scheme D provides a general synthetic scheme for preparing compounds of formula (2) wherein n=0.

In step a, the appropriate phenol of structure (24) is nitrated to give the corresponding 4-hydroxy-nitrobenzene of structure (25).

For example, the appropriate phenol of structure (24) is contacted with a molar excess of a nitrating agent, such as nitronium tetrafluoroborate. The reactants are typically contacted in a suitable organic solvent, such as methylene chloride. The reactants are typically stirred together for a period of time ranging from 10–50 hours and at a temperature range of from −60° C. to 10° C. The 4-hydroxy-nitrobenzene of structure (25) is recovered from the reaction mixture by extractive methods as is known in the art. They can be separated by silica gel chromatography.

In step b, the nitro functionality of an appropriate 4-hydroxy-nitrobenzene of structure (25) is reduced to give the corresponding 4-hydroxy-aniline of structure (26).

For example, an appropriate 4-hydroxy-nitrobenzene of structure (25) is contacted with a catalytic amount of a hydrogenation catalyst, such as 10% palladium/carbon. The reactants are typically contacted in a suitable solvent mixture such as tetrahydrofuran/water. The reactants are typically shaken under a hydrogen atmosphere of 35–45 psi at room temperature for a period of time ranging from 5–24 hours. The 4-hydroxy-aniline of structure (26) is recovered from the reaction zone by evaporation as the solvent. It can be purified by silica gel chromatography.

In step c, the aniline functionality of 4-hydroxyaniline of structure (26) is converted to the corresponding 4-hydroxy-N-[4-methylphenyl)sulfonyl]-aniline of structure (27).

For example, the appropriate 4-hydroxy-aniline of structure (26) is contacted with a slight molar excess of p-toluenesulfonyl chloride. The reactants are typically contacted in an organic base such as anhydrous pyridine. The reactants are typically stirred together for a period of time ranging from 2–24 hours and at a temperature range of from 5° C. to room temperature. The 4-hydroxy-N-[(4-methylphenyl)sulfonyl]-aniline of structure (27) is recovered from the reaction zone by extractive methods as is known in the art. It can be purified by silica gel chromatography.

In step d, the appropriate 4-hydroxy-N-[(4-methylphenyl)sulfonyl]-aniline of structure (27) is alkylated with an appropriate bis(hydroxyalkyl)-t-butylcarboxamide of structure (17) to give the appropriate bis[4-hydroxyphenyl]-bis[N-(4-methylphenyl)sulfonyl]-(t-butyloxycarbonyl)-triazaalkane of structure (28).

For example, the appropriate 4-hydroxy-N-[(4-methylphenyl)sulfonyl]-aniline of structure (27) is contacted with a molar excess of triphenylphosphine, a one-half molar equivalent of the appropriate bis(hydroxyalkyl)t-butylcarboxamide of structure (17) and a molar excess of diethyl azodicarboxylate. The reactants are typically contacted in a suitable organic solvent such as tetrahydrofuran. The reactants are typically stirred together at room temperature for a period of time ranging from 2–24 hours. The bis[4-hydroxyphenyl]-bis[N-(4-methylphenyl)sulfonyl]-(t-butyloxycarbonyl)-triazaalkane of structure (28) is recovered from the reaction zone by evaporation of the solvent. It can be purified by silica gel chromatography.

In step e, the sulfonamide functionalities of the appropriate bis[4-hydroxyphenyl]-bis[N-(4-methylphenyl)sulfonyl]-(t-butyloxycarbonyl)-triazaalkane of structure (28) are cleaved to give the appropriate bis[4-hydroxyphenyl]-(t-butyloxycarbonyl)-triazaalkane of structure (29) as described previously in Scheme A, step d.

In step f, the t-butyloxycarbonyl functionality of the appropriate bis[4-hydroxyphenyl]-(t-butyloxycarbonyl)triazaalkane of structure (29) is hydrolyzed to give the appropriate bis[4-hydroxyphenyl]-triazaalkane of structure (30) as described previously in Scheme A, step c.

Starting materials for use in Scheme D are readily available to one of ordinary skill in the art.

The following example presents a typical synthesis as described in Scheme D. This example is illustrative only and is not intended to limit the scope of the present invention in any way.

EXAMPLE 4

1,9-Bis[3,5-di-t-butyl-4-hydroxyphenyl]-1,5,9-triazanonane, trihydrochloride

Step a: 3,5-Di-t-butyl-4-hydroxy-nitrobenzene

Dissolve 2,6-di-t-butylphenol (721 mg, 3.5 mmol) in methylene chloride (10 mL) and cool to −60° C. Add, by dropwise addition, a solution of nitronium tetrafluoroborate (25 mL of a 0.5M solution in sulfolane, 12.5 mmol) in methylene chloride (15 mL). Warm slowly to 10° C. and partition between methylene chloride (75 mL) and water (75 mL). Separate the aqueous phase and extract with methylene chloride (50 mL). Combine the organic phases, dry (MgSO$_4$) and evaporate the solvent in vacuo. Purify and separate by flash silica gel chromatography to give the title compound.

Step b: 3,5-Di-t-butyl-4-hydroxy-aniline, hydrochloride

Dissolve 3,5-di-t-butyl-4-hydroxy-nitrobenzene (17.3 mg, 0.069 mmol) in tetrahydrofuran (6 mL). Add 10% palladium/carbon (20 mg) and water (3 mL). Shake under 45 psi of hydrogen at room temperature for 5 hours. Filter and partition the filtrate between in 1N hydrochloric acid and methylene chloride. Separate the aqueous phase and freeze dry to give the title compound.

Step c: 3,5-Di-t-butyl-4-hydroxy-N-[(4-methylphenyl)sulfonyl]-aniline

Dissolve 3,5-di-t-butyl-4-hydroxy-aniline (2.21 g, 10 mmol) in anhydrous pyridine (25 mL) and cool to 5° C. Add, by dropwise addition, p-toluenesulfonyl chloride (2.1 g, 11 mmol) and stir overnight. Partition between water and ethyl acetate and separate the organic phase. Wash the organic phase with cold 1N hydrochloric acid, saturated sodium hydrogen carbonate and brine. Dry (MgSO$_4$) and evaporate the solvent in vacuo to give the title compound.

Step d: 1,9-Bis[3,5-di-t-butyl-4-hydroxyphenyl]-1,9-bis[N-(4-methylphenyl)sulfonyl]-5-(t-butyloxycarbonyl)-1,5,9-triazanonane Dissolve bis(3-hydroxypropyl)amine (1.33 g, 10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3X), dry (MgSO$_4$) and evaporate the solvent in vacuo. Purify the residue by silica gel chromatography to give bis(3-hydroxypropyl)-t-butylcarboxamide. Dissolve 3,5-di-t-butyl-4-hydroxy-N-[(4-methylphenyl)sulfonyl]-aniline (142 mg, 0.43 mmol) in anhydrous tetrahydrofuran (3 mL) and add triphenylphosphine (168 mg, 0.645 mmol). Stir under a nitrogen atmosphere and add bis(3-hydroxypropyl)-t-butylcarboxamide (83.6 mg, 0.215 mmol) followed by diethyl azodicarboxylate (0.083 mL, 0.530 mmol). Stir at room temperature for several hours and evaporate the solvent in vacuo. Purify by silica gel chromatography to give the title compound.

Step e:
1,9-Bis[3,5-di-t-butyl-4-hydroxyphenyl]-5-(t-butyloxycarbonyl)-1,5,9-triazanonane Mix 1,9-bis[3,5-di-t-butyl-4-hydroxyphenyl]-1,9-bis[N-(4-methylphenyl)sulfonyl]-5-(t-butyloxycarbonyl)-1,5,9-triazanonane (946 mg, 1 mmol) in dry liquid ammonia (25 mL) at −40° C. Add small pieces of sodium until a permanent blue color remains. Discharge the excess sodium with saturated ammonium chloride. Allow the ammonia to evaporate spontaneously and partition the residue between ethyl acetate and water Separate the organic phase, dry (MgSO$_4$) and evaporate the solvent in vacuo. Purify by silica gel chromatography to give the title compound.

Step f:
1,9-Bis[3,5-di-t-butyl-4-hydroxyphenyl]-1,5,9-triazanonane, trihydrochloride Dissolve 1,9-bis[3,5-di-t-butyl-4-hydroxyphenyl]-5-(t-butyloxycarbonyl)-1,5,9-triazanonane (6.39 g, 10 mmol) in saturated methanolic hydrochloric acid (100 mL). Stir for several hours and evaporate the solvent in vacuo to give the title compound.

The following compounds may be prepared analogously to that described in Example 4:
1,11-Bis[3,5-di-t-butyl-4-hydroxyphenyl]-1,6,11-triazaundecane, trihydrochloride;
1,15-Bis[3,5-di-t-butyl-4-hydroxyphenyl]-1,8,15-triazapentadecane, trihydrochloride.

The present invention provides a method of protecting cells from deleterious cellular effects caused by exposure to ionizing radiation or by exposure to a DNA-reactive agent.

Ionizing radiation is high energy radiation, such as an X-ray or a gamma ray, which interacts to produce ion pairs in matter. Exposure to ionizing radiation may occur as the result of environmental radiation, such as resulting from a nuclear explosion, a spill of radioactive material, close proximity to radioactive material and the like. More commonly, exposure to ionizing radiation may occur as the result of radiological medical procedures such as radiation therapy for various types of cancers.

DNA-reactive agents are those agents, such as alkylating agents, cross-linking agents, and DNA intercalating agents, which interact covalently or non-covalently with cellular DNA causing certain deleterious cellular effects. For example, DNA-reactive agents include cisplatin, cyclophosphamide, diethylnitrosoamine, benzo(a)pyrene, carboplatin, doxorubicin, mitomycin-C and the like. Many of these DNA-reactive agents, such as cisplatin, cyclophosphamide, doxorubicin and mitomycin-C are useful in cancer therapy as DNA-reactive chemotherapeutic agents.

Deleterious cellular effects caused by exposure to ionizing radiation or to a DNA-reactive agent include damage to cellular DNA, such as DNA strand break, disruption in cellular function, such as by disrupting DNA function, cell death, tumor induction, such as therapy-induced secondary tumor induction, and the like. These deleterious cellular effects can lead to secondary tumors, bone marrow suppression, kidney damage, peripheral nerve damage, gastrointestinal damage and the like. For example, in cancer radiation therapy, the exposure to radiation is intended to cause cell death in the cancer cells. Unfortunately, a large part of the adverse events associated with the therapy is caused by these deleterious cellular effects of the radiation on normal cells as opposed to cancer cells.

The present invention provides a method by which cells are protected from deleterious cellular effects by preventing or eliminating these effects or by reducing their severity. According to the present invention, the cells to be protected are contacted with a compound of formula (1) or (2) prior to or during exposure of the cell to ionizing radiation or to DNA-reactive agents. The cells may be contacted directly, such as by applying a solution of a compound of the invention to the cell or by administering a compound of the invention to a mammal. The compounds of the present invention thus provide a protective effect in the cell which eliminates or reduces the severity of the deleterious cellular effects which would otherwise be caused by the exposure.

More particularly, the present invention provides a method of protecting non-cancer, or normal, cells of a mammal from deleterious cellular effects caused by exposure of the mammal to ionizing radiation or to a DNA-reactive agent. As used herein, the term "mammal" refers to warmblooded animals such as mice, rats, dogs and humans. The compounds of the present invention provide a selective protection of normal cells, and not of cancer cells, during cancer radiation therapy and during chemotherapy with a DNA-reactive chemotherapeutic agent. According to the present invention the compound of the invention is administered to the mammal prior to or during exposure to ionizing radiation or to a DNA-reactive agent. The present invention provides a method whereby the deleterious cellular effects on non-cancer cells caused by exposure of the mammal to ionizing radiation or to a DNA-reactive agent are eliminated or reduced in severity or in extent.

In addition, the present invention provides a method of treating a patient in need of radiation therapy or in need of chemotherapy with a DNA-reactive chemotherapeutic agent. As used herein, the term "patient" refers to a mammal, including mice, rats, dogs and humans, which is afflicted with a neoplastic disease state or cancer such that it is in need of cancer radiation therapy or chemotherapy with a DNA-reactive chemotherapeutic agent. The term "neoplastic disease state" as used herein refers to an abnormal state or condition characterized by rapidly proliferating cell growth or neoplasm.

Neoplastic disease states for which treatment with a compound of formula (1) or (2) will be particularly useful in conjunction with radiation therapy or chemotherapy with a DNA-reactive chemotherapeutic agent include: Leukemias such as, but not limited to, acute lymphoblastic, acute myelogenous, chronic lymphocytic, acute myeloblastic and chronic myelocytic; Carcinomas, such as, but not limited to, those of the cervix, oesophagus, stomach, pancreas, breast, ovaries, small intestines, colon and lungs; Sarcomas, such as, but not limited to, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma, Hodgkin's disease and non-Hodgkin's lymphoma. Neoplastic disease states for which treatment with a compound of formula (1) or (2) will be particularly preferred in conjunction with radiation therapy or chemotherapy include Hodgkin's disease, pancreatic carcinoma, advanced carcinoma, breast cancers, ovarian cancer, colon cancers and the like.

In addition, treatment with a compound of the present invention provides selective protection against deleterious cellular effects, such as therapy-induced secondary tumor induction, caused by radiation therapy or chemotherapy with a DNA-reactive chemotherapeutic agent. Treatment with a compound of the present invention is thus useful in eliminating or reducing the risk of secondary tumor induction, such as therapy-induced acute myelogenous leukemia and non-Hodgkin's lymphoma, brought about by radiotherapy or chemotherapy for treatment of Hodgkin's disease.

According to the present invention, administration to a patient of a compound of formula (1) or (2) prior to or during radiation therapy or chemotherapy with a DNA-reactive chemotherapeutic agent will provide a selective protection of non-cancer cells of the patient but not of cancer cells. The deleterious cellular effects on non-cancer cells caused by treatment of the patient with ionizing radiation or with a DNA-reactive chemotherapeutic agent are thus eliminated or reduced in severity or in extent.

A protective amount of a compound of formula (1) or (2) refers to that amount which is effective, upon single or multiple dose administration to a mammal or patient, in eliminating or reducing in severity or in extent the deleterious cellular effects caused by exposure to or treatment with ionizing radiation or a DNA-reactive agent. A protective amount of a compound of formula (1) or (2) also refers to that amount which is effective, upon single or multiple dose administration to the cell, in eliminating or reducing in severity or in extent the deleterious cellular effects caused by exposure to ionizing radiation or a DNA-reactive agent.

A protective amount for administration to a mammal or a patient can be readily determined by the attending diagnostician, as one skilled in the art, by the use of known techniques and by observing results obtained under analogous circumstances. In determining the protective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

The compounds of formula (1) or (2) may be administered as single doses or as multiple doses and are ordinarily administered prior to and/or during exposure to ionizing radiation or to DNA-reactive agents. Generally, where a compound of the present invention is administered in conjunction with radiation therapy, the compound of the present invention will be administered in single or multiple doses prior to radiation therapy following a schedule calculated to provide the maximum selective protective effect during radiation therapy. Generally, where a compound of the present invention is administered in conjunction with a DNA-reactive chemotherapeutic agent, the compound of the present invention will be administered in single or multiple doses prior to and during chemotherapy following a schedule calculated to provide the maximum selective protective effect during chemotherapy.

The details of the dosing schedule for the compounds of the present invention necessary to provide the maximum selective protective effect upon exposure to ionizing radiation or to a DNA-reactive agent can be readily determined by an attending physician, as one skilled in the art, by the use of known techniques and by observing results obtained under analogous circumstances.

A protective amount of a compound of formula (1) or (2) for administration to a mammal or patient will vary from about 5 milligram per kilogram of body weight per day (mg/kg/day) to about 1000 mg/kg/day. Preferred amounts are expected to vary from about 50 to about 500 mg/kg/day.

A protective amount of a compound of formula (1) or (2) for contacting a cell will vary from about 100 micromolar to about 5 millimolar in concentration.

A compound of formula (1) or (2) can be administered to a mammal or a patient in any form or mode which makes the compound bioavailable in effective amounts, including oral and parenteral routes. For example, compounds of formula (1) and (2) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (1) or (2) in admixture or otherwise in association with one or more inert carriers. These compositions are useful, for example, as assay standards, as convenient means of making bulk shipments, or as pharmaceutical compositions. An assayable amount of a compound of formula (1) or (2) is an amount which is readily measurable by standard assay procedures and techniques as are well known and appreciated by those skilled in the art. Assayable amounts of a compound of formula (1) or (2) will generally vary from about 0.001% to about 75% of the composition by weight. Inert carriers can be any material which does not degrade or otherwise covalently react with a compound of formula (1) or (2). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (1) or (2) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel ™, corn starch and the like; lubricants such as magnesium stearate or Sterotex ™; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (1) or (2) in their end-use application.

Compounds of formula (1) wherein $R_1$ and $R_2$ are each t-butyl or isopropyl are generally preferred. Compounds of formula (1) wherein n is 1 or 2 are generally preferred. Compounds of formula (1) wherein Z is a $C_3$ or $C_4$ alkylene group are generally preferred. Compounds of formula (1) wherein m is 6, 7 or 8 are generally preferred.

Compounds of formula (2) wherein $R_1$ and $R_2$ are each t-butyl are generally preferred. Compounds of formula (1) wherein n is 1 or 2 are generally preferred. Compounds of formula (1) wherein Z is a $C_3$ or $C_4$ alkylene group are generally preferred.

The utility of the compounds of the present invention may be demonstrated as radioprotective agents both in vitro and in vivo. The following studies illustrate the utility of the compounds of formula (1). These studies are understood to be illustrative only and are not intended to limit the scope of the invention in any way. As used herein the following terms have the indicated meaning; KeV refers to units of one thousand electron volts; Rads is a unit of absorbed dose in living systems of energy from ionizing radiation; mm is an area term and refers to millimeters; μM is a concentration term and refers to micromolar; MEM is a culture media term and refers to Minimal Essential Medial.

For example, the ability of cultured cells to form clones (colonies) may be evaluated as a function of exposure to X-ray dose or chemical dose. Cells are either not drug treated or are treated with a test agent 30 minutes prior to exposure. The degree of retention of ability to form clones after exposure, in comparison to untreated cells, is directly related to the protective effect of the drug. A typical experiment of this type may be carried out essentially as described by Snyder and Lachmann [*Radiation Res.* 120, 121 (1989)].

In Vitro Radioprotection

Cultured human cervical carcinoma cells are plated, grown and maintained in 60mm tissue culture dishes in standard MEM media supplemented with 10% fetal bovine serum. The density of cells at the time of treatment should be between 2 and $6 \times 10^5$ cells per dish. Cultures are either not drug treated or are treated with test compound for 30 minutes in complete media at 37° C. Cultures, in the continued presence of drug-containing medium are then X-irradiated over a dose range of 0 to 2400 Rads in a TfI Bigshot cabinet-type X-ray unit set at 50 Kev and delivering approximately 160 Rads per minute as determined by dosimeter.

Colony forming ability studies are then conducted. The cultures are covered with 1.0 ml of trypsin for 3 minutes, the trypsin is removed and replaced with 1.0 ml MEM, and the cells are scraped from the dish with a cell scraper. An aliquot is taken for the determination of cell number by coulter counter analysis. An appropriate number of cells is then taken from each culture for reseeding so that between 50 and 4000 colonies arise. As an example, unirradiated cultures might be reseeded at 500 cells/dish while cultures receiving 1600 Rads would be reseeded at 30,000 cells/dish. Seeded 60 mm tissue culture dishes are then incubated for 10 days for colony formation. Colonies are then distinguished by methanol rinse, Dif-Quik staining and they are then counted manually under magnification.

Colony forming ability is represented as a percentage of those plated cells which are able to grow into a colony of greater than 50 cells. Unirradiated HeLa cells usually display a 40-70% ability to form colonies. The number of colonies formed in irradiated or drug-treated irradiated cultures is compared to the appropriate unirradiated or drug-treated unirradiated control in order to determine the percent colony forming ability. In general, these studies would be conducted with the highest dose of drug previously shown not to cause significant toxicity with this treatment protocol. Thus data are interpreted by comparing the survival curves from untreated and drug treated cultures over the X-ray dose range employed and the dose of X-rays required to inhibit colony forming ability by 37% ($ID_{37}$) is determined. The results for 1,9-Bis[(3,5-di-t-butyl-4-hydroxyphenyl)methyl]-1,5,9-triazanonane were; $ID_{37}$ control=750 Rads, $ID_{37}$(1 uM drug)=1100 Rads.

Alternatively, the production of DNA strand breaks upon exposure to X-ray dose or chemical dose may be evaluated. Cells are either not drug treated or are treated with a test agent about 30 minutes prior to exposure. The extent of DNA strand breakage after exposure, in comparison to that in untreated cells, is inversely related to the protective effect of the drug. A typical experiment of this type may be carried out essentially as described by Snyder [*Int. J. Radiat. Biol.* 55, 773 (1989)].

In Vivo Radioprotection

The survivability of mice exposed to whole body irradiation or to a DNA-reactive agent may be evaluated. Animals, either pre-treated with a test agent or untreated (Control Group), are exposed to whole body irradiation (1500 rads). Untreated control animals are expected to survive about 12-15 days. The degree of survivability of the treated animals, in comparison to the untreated controls, is directly related to the protective effect of the drug treatment. A typical experiment of this type may be carried out essentially as described by Carroll et al. [*J. Med. Chem.* 33., 2501 (1990)].

The ability of a test compound to protect mice against the lethal effects of whole body X-irradiation may be tested by giving a single i.p. injection of drug 30 minutes prior to X-irradiation. Following drug administration, test animals are irradiated for 10 minutes at 90 Kev on the top shelf of the TFI Bigshot cabinet-type X-ray unit. Following irradiation the animals are returned to their cages and their survival is monitored. A test group will usually consist of 6-8 mice. The day of death for each member of a group is noted and an average survival value is calculated. This value is compared to that of the non-drug treated control included in the experiment. The results for 1,9-Bis[(3,5-di-t-butyl-4-hydroxyphenyl)methyl]-1,5,9-triazanonane, trihydrochloride were; Experiment No. 1 control group survival 19.7 da.±2.3 n=4, test group survival (1 mg/kg) 25.8±7.0 n=4. Experiment No. 2 control survival=21.6±3.5 n=9, test group survival (2 mg/kg)>42.5 n=9.

The production of DNA strand breaks in lymphocytes taken from treated animals exposed to whole body irradiation or to a DNA-reactive agent may be evaluated in comparison to untreated control. Alternatively, the viability and clonogenicity of bone marrow cells taken from treated animals exposed to whole body irradiation or to a DNA-reactive agent may be evaluated in comparison to untreated control as described by Pike and Robinson [*J. Cell Physiol.* 76, 77 (1970)].

What is claimed is:

1. A compound of the formula

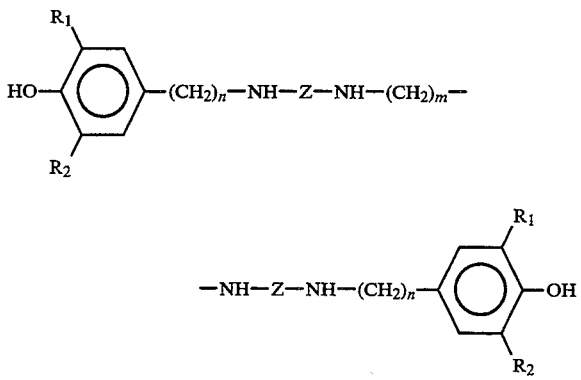

wherein
$R_1$ and $R_2$ are each independently a $C_1$-$C_6$ alkyl group,
n is an integer from 0 to 3,
Z is a $C_2$-$C_6$ alkylene group, and
m is an integer from 4 to 9.

2. A compound of the formula

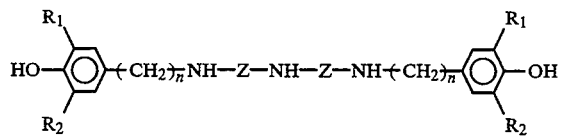

wherein
$R_1$ and $R_2$ are each independently a $C_1$-$C_6$ alkyl group,
n is an integer from 0 to 3, and
Z is a $C_2$-$C_6$ alkylene group.

3. A method of protecting mammalian cells from deleterious cellular effects caused by exposure to ionizing radiation comprising contacting said cells with a protective amount of a compound of claim 1 or 2.

4. A method of protecting mammalian cells from deleterious cellular effects caused by exposure to a DNA-reactive agent comprising contacting said cells with a protective amount of a compound of claim 1 or 2.

5. A method of protecting non-cancer cells of a human from deleterious cellular effects caused by exposure to ionizing radiation comprising administering to said human a protective amount of a compound of claim 1 or 2.

6. A method of protecting non-cancer cells of a human from deleterious cellular effects caused by exposure to a DNA-reactive agent comprising administering to said human a protective amount of a compound of claim 1 or 2.

7. A method of treating a patient in need of radiation therapy comprising administering to said patient a protective amount of a compound of claim 1 or 2.

8. A method of treating a patient in need of chemotherapy with a DNA-reactive chemotherapeutic agent comprising administering to said patient a protective amount of a compound of claim 1 or 2.

9. A composition comprising a compound of claim 1 or 2 in admixture or otherwise in association with an inert carrier.

10. A pharmaceutical composition comprising a protective amount of a compound of claim 1 or 2 in admixture or otherwise in association with one or more pharmaceutically acceptable carriers or excipients.

11. A compound of claim 1 wherein the compound is 1,19-bis[(3,5-di-t-butyl-4-hydroxyphenyl)methyl]-1,6,14,19-tetraazanonadecane.

12. A compound of claim 1 wherein the compound is 1,15-bis[(3,5-di-t-butyl-4-hydroxyphenyl)]-1,5,11,15-tetraazapentadecane.

13. A compound of claim 2 wherein the compound is 1,9-bis[(3,5-di-t-butyl-4-hydroxyphenyl)methyl]-1,5,9-triazanonane.

14. A compound of claim 2 wherein the compound is 1,9-bis[3,5-di-t-butyl-4-hydroxyphenyl]-1,5,9-triazanonane.

* * * * *

UNITED STATES PATENT AND TRADEMARK OFFICE
CERTIFICATE OF CORRECTION

PATENT NO.   : 5,354,782
DATED        : October 11, 1994
INVENTOR(S)  : Michael L. Edwards, Ronald D. Snyder

It is certified that error appears in the above-identified patent and that said Letters Patent is hereby corrected as shown below:

Column 5, Line 39 patent reads " his [" and should read -- bis [ --.

Column 7, Line 33 patent reads " vacuo" and should read -- in vacuo --.

Column 10, Line 48 patent reads " (4-" and should read -- [ ( 4- --.

Column 15, Line 35 patent reads " H7S" and should read -- H7g --.

Column 19, Line 12 patent reads " water" and should read -- water. --.

Signed and Sealed this

Ninth Day of April, 1996

Attest:

BRUCE LEHMAN

*Attesting Officer*      *Commissioner of Patents and Trademarks*